US010705005B2

United States Patent
Qi et al.

(10) Patent No.: US 10,705,005 B2
(45) Date of Patent: Jul. 7, 2020

(54) UNIT FOR VALIDATING IN SITU DECONTAMINATION EFFECT AND DEVICE FOR FILTERING BIOLOGICALLY CONTAMINATED AIR TO WHICH THE UNIT IS APPLIED

(71) Applicant: Institute of Medical Equipment, Academy of Military Medical Sciences, PLA, Tianjin (CN)

(72) Inventors: Jiancheng Qi, Tianjin (CN); Zongxing Zhang, Tianjin (CN); Ying Yi, Tianjin (CN); Jinhui Wu, Tianjin (CN)

(73) Assignee: Institute of Medical Equipment, Academy of Military Medical Sciences, PLA, Tianjin (CN)

( * ) Notice: Subject to any disclaimer, the term of this patent is extended or adjusted under 35 U.S.C. 154(b) by 249 days.

(21) Appl. No.: 15/917,364

(22) Filed: Mar. 9, 2018

(65) Prior Publication Data
US 2019/0137378 A1 May 9, 2019

(30) Foreign Application Priority Data

Nov. 9, 2017 (CN) .......................... 2017 1 1094344

(51) Int. Cl.
*B01D 35/30* (2006.01)
*G01N 15/08* (2006.01)
(Continued)

(52) U.S. Cl.
CPC ............ *G01N 15/082* (2013.01); *A61L 9/015* (2013.01); *B01D 35/143* (2013.01); *B01D 35/30* (2013.01);
(Continued)

(58) Field of Classification Search
CPC ...... B01D 35/00; B01D 35/143; B01D 35/30; G01N 15/082; A61L 2/22
(Continued)

(56) References Cited

U.S. PATENT DOCUMENTS 10,517,977 B2 * 12/2019 Sakaki ...................... A61L 2/20

OTHER PUBLICATIONS

U.S. Department of Health and Human Services, Public Health Service, Centers for Disease Control and Prevention, National Institutes of Health, Biosafety in Microbiological and Biomedical Laboratories, 5th Edition, revised Dec. 2009, 438 pages.

* cited by examiner

*Primary Examiner* — Robert A Hopkins
(74) *Attorney, Agent, or Firm* — Hanley, Flight and Zimmerman, LLC (57) ABSTRACT

The present invention discloses a unit for validating an in situ decontamination effect, including a connecting end. A left end of the connecting end is in communication with any space that needs gas decontamination. A right end of the connecting end is connected to a closed isolation damper. A right end of the closed isolation damper is connected to a hollow decontamination validation chamber. A sealing cover is sleeved over an outer wall of the decontamination validation chamber. A mesh cup is placed inside the decontamination validation chamber, and the mesh cup is used for placing a bioindicator. In addition, the present invention further discloses a device for filtering biologically contaminated air, including a unit for validating an in situ decontamination effect and a hollow box installed with a high efficiency particulate air (HEPA) filter. The unit for validating an in situ decontamination effect is in communication with the hollow box. In the present invention, an actual decontamination effect of the HEPA filter after gas decontamination can be validated reliably in time, thereby effec- (Continued)

tively preventing pathogenic microorganisms that exist on the surface of the HEPA filter from spreading to the external environment, avoiding polluting the external environment, and ensuring personal safety.

18 Claims, 5 Drawing Sheets

(51) Int. Cl.
  *G01N 21/77* (2006.01)
  *B01D 46/00* (2006.01)
  *B01D 46/24* (2006.01)
  *F24F 3/16* (2006.01)
  *F24F 13/20* (2006.01)
  *C12Q 1/22* (2006.01)
  *A61L 9/015* (2006.01)
  *B01D 35/143* (2006.01)

(52) U.S. Cl.
  CPC ......... *B01D 46/0028* (2013.01); *B01D 46/24* (2013.01); *C12Q 1/22* (2013.01); *F24F 3/1603* (2013.01); *F24F 13/20* (2013.01); *G01N 21/77* (2013.01); *A61L 2209/14* (2013.01); *B01D 2279/65* (2013.01); *G01N 2015/084* (2013.01); *G01N 2021/775* (2013.01)

(58) Field of Classification Search
  USPC ...................................... 96/417; 55/467, 471
  See application file for complete search history.

UNIT FOR VALIDATING IN SITU DECONTAMINATION EFFECT AND DEVICE FOR FILTERING BIOLOGICALLY CONTAMINATED AIR TO WHICH THE UNIT IS APPLIED

This application claims priority to Chinese application number 201711094344.3, filed 9 Nov. 2017, with a title of UNIT FOR VALIDATING IN SITU DECONTAMINATION EFFECT AND DEVICE FOR FILTERING BIOLOGICALLY CONTAMINATED AIR TO WHICH THE UNIT IS APPLIED. The above-mentioned patent application is incorporated herein by reference in its entirety.

TECHNICAL FIELD

The present invention relates to the technical field of biosafety protection and equipment, and in particular, to a unit for validating an in situ decontamination effect and a device for filtering biologically contaminated air to which the unit is applied.

BACKGROUND

Pathogenic microorganisms are microorganisms that cause diseases in humans and animals, and easily produce infections or even infectious diseases. During operations such as tests and experiments on pathogenic microorganisms, hazardous biological aerosols are formed easily. If the hazardous biological aerosols scatter outside a laboratory, the environment in and around the laboratory will be severely polluted and a major public health event will be caused. Therefore, to ensure personal safety, contaminated air discharged by a biosafety facility such as a laboratory needs to be filtered.

Currently, a high efficiency particulate air (HEPA) filter is usually used to filter contaminated air discharged by a biosafety facility such as a laboratory. The HEPA filter serves as one of the most important secondary barriers, and is a main technical measure to prevent hazardous particles in the air inside the biosafety facility such as a laboratory from entering the outdoor environment.

Currently, the bacterial filtration efficiency of a HEPA filter is close to 100%. However, pathogenic microorganisms captured by the HEPA filter are very likely to survive and multiply under suitable temperature and humidity conditions. That is, there is a risk that pathogenic microorganisms may survive and multiply on the surface of the HEPA filter. Currently, a decontamination method using gaseous or vaporous fumigation is mainly used to perform further gas decontamination on the HEPA filter, so as to eliminate pathogenic microorganisms that exist on the surface of the HEPA filter.

However, an actual decontamination effect of the existing decontamination method using gas fumigation depends on various factors such as the type of a disinfectant, the dosage of a disinfectant, a decontamination volume, the temperature of a decontamination object, the humidity of a decontamination object, the decontamination effect time, and the permeation of a disinfectant in a filtering material. As a result, the decontamination effect of the decontamination method is relatively unpredictable, which easily causes great potential safety hazards to the replacement of a HEPA filter and other tests and maintenance.

For this, the validation of a decontamination effect becomes a critical step to ensure that a requirement of in situ gas decontamination is met. Currently, some international standards set out clear requirements. For example, Biosafety in Microbiological and Biomedical Laboratories (5th) from the United States Centers for Disease Control and Prevention (CDC) requires that the HEPA filter housings should be designed to allow for in situ decontamination and validation of the filter prior to removal.

Therefore, currently, there is an urgent need to develop a device that can reliably validate a decontamination effect of a HEPA filter in time, thereby effectively preventing pathogenic microorganisms that exist on the surface of the HEPA filter from spreading outside a biosafety facility such as a laboratory, avoiding polluting the external environment of the biosafety facility such as a laboratory, and ensuring personal safety.

SUMMARY

In view of this, the objective of the present invention is to provide a unit for validating an in situ decontamination effect and a device for filtering biologically contaminated air to which the unit is applied, so as to reliably validate in time an actual decontamination effect of a HEPA filter after gas decontamination, thereby effectively preventing pathogenic microorganisms that exist on the surface of the HEPA filter from spreading outside a biosafety facility such as a laboratory, avoiding polluting the external environment of the biosafety facility such as a laboratory, ensuring personal safety, and eliminating the possibility of a major public health event, which is greatly significant in production practice.

For this, the present invention provides a unit for validating an in situ decontamination effect, including a connecting end, where a left end of the connecting end is in communication with any space that needs gas decontamination;

a right end of the connecting end is connected to a closed isolation damper, a right end of the closed isolation damper is connected to a hollow decontamination validation chamber, and a sealing cover is sleeved over an outer wall of the decontamination validation chamber; and the decontamination validation chamber is used for placing a bioindicator.

A mesh cup is placed inside the decontamination validation chamber, and the mesh cup is used for placing the bioindicator.

In addition, the present invention provides a device for filtering biologically contaminated air, including a unit for validating an in situ decontamination effect and a hollow box installed with a HEPA filter, where the unit for validating an in situ decontamination effect is in communication with the hollow box.

The hollow box is a tuyere box, and the tuyere box includes a first chamber and a second chamber that are transversely distributed.

The HEPA filter is disposed on an inner side at the bottom of the first chamber, and the HEPA filter is in communication with an external space that needs air filtering; and the unit for validating an in situ decontamination effect is installed on a left sidewall of the second chamber, the unit for validating an in situ decontamination effect is in communication with the first chamber, and the unit for validating an in situ decontamination effect is configured to validate a decontamination effect of the HEPA filter that needs to perform gas decontamination.

An air inlet is provided at the bottom of the HEPA filter, an air outlet is provided at the top of the HEPA filter, and high-efficiency filter media are spaced apart between the air inlet and the air outlet; and a vent hole is opened at a position corresponding to the air inlet on a bottom surface of the first chamber, and the vent hole and the air inlet are in communication with the external space that needs air filtering.

An air outlet is provided at the top of the first chamber, and the air outlet is in communication with an isolation damper.

The unit for validating an in situ decontamination effect is in communication with a right-side inner wall of the first chamber.

The unit for validating an in situ decontamination effect includes a connecting end, where a left end of the connecting end is in communication with the right-side inner wall of the first chamber, a right end of the connecting end is connected to a closed isolation damper, a right end of the closed isolation damper is connected to a hollow decontamination validation chamber, and a sealing cover is sleeved over an outer wall of the decontamination validation chamber.

A mesh cup is placed inside the decontamination validation chamber, and the mesh cup is used for placing a bioindicator.

The left sidewall of the second chamber is further in communication with a first gas decontamination tube, a left end of the first gas decontamination tube is in communication with the first chamber, a right end of the first gas decontamination tube is in communication with an upper end of a second gas decontamination tube through a first gas decontamination interface, a lower end of the second gas decontamination tube is in communication with an air circulation drive device, and the air circulation drive device is located in the external space that needs air filtering; and the air circulation drive device is a fan or an air pump.

The hollow box is a box body, and a left end and a right end of the box body are respectively in communication with an airtight isolation damper;

the HEPA filter is disposed on a front surface in the middle of the box body; and a second gas decontamination joint outlet and a second gas decontamination joint inlet are further respectively disposed at positions on a left side and a right side of the HEPA filter of the front surface of the box body, and one unit for validating an in situ decontamination effect is further disposed at a position below the second gas decontamination joint inlet on the front surface of the box body.

As can be seen from the foregoing technical solutions provided in the present invention, compared with the prior art, the present invention provides a unit for validating an in situ decontamination effect and a device for filtering biologically contaminated air to which the unit is applied, so as to validate reliably in time an actual decontamination effect of a HEPA filter after gas decontamination, thereby effectively preventing pathogenic microorganisms that exist on the surface of the HEPA filter from spreading outside a biosafety facility such as a laboratory, avoiding polluting the external environment of the biosafety facility such as a laboratory, ensuring personal safety, and eliminating the possibility of a major public health event, which is greatly significant in production practice.

In addition, by means of the unit for validating an in situ decontamination effect and the device for filtering biologically contaminated air to which the unit is applied provided in the present invention, a decontamination effect of a HEPA filter after gas decontamination can be validated reliably in time, and at the same time the function of performing in situ gas decontamination on the HEPA filter is further provided, so as to effectively perform gas decontamination on the HEPA filter and synchronously implement the decontamination of a biosafety facility such as a laboratory connected to the HEPA filter.

In the figures: 1 is a tuyere box, 2 is a HEPA filter, 3 is an isolation damper, 4 is a first gas decontamination interface, 5 is an air circulation drive device, 61 is a first gas decontamination tube, 62 is a second gas decontamination tube, 7 is a gas disinfectant, 8 is a connecting end, 9 is a closed isolation damper, 10 is a decontamination validation chamber, 11 is a mesh cup, 12 is a sealing cover, 13 is a bioindicator;

21 is a first chamber, 22 is a second chamber, 100 is a unit for validating an in situ decontamination effect, 14 is a box body, 15 is a second gas decontamination joint inlet, 16 is a second gas decontamination joint outlet, and 17 is an airtight isolation damper.

DETAILED DESCRIPTION

To enable a person skilled in the art to better understand the present invention, the present invention is further described below in detail with reference to the accompanying drawings and implementation manners.

Referring to FIG. 1 to FIG. 5, the present invention provides a device for filtering biologically contaminated air, including a tuyere box 1, and the tuyere box 1 includes a first chamber 21 and a second chamber 22 that are transversely distributed.

Figure 1:
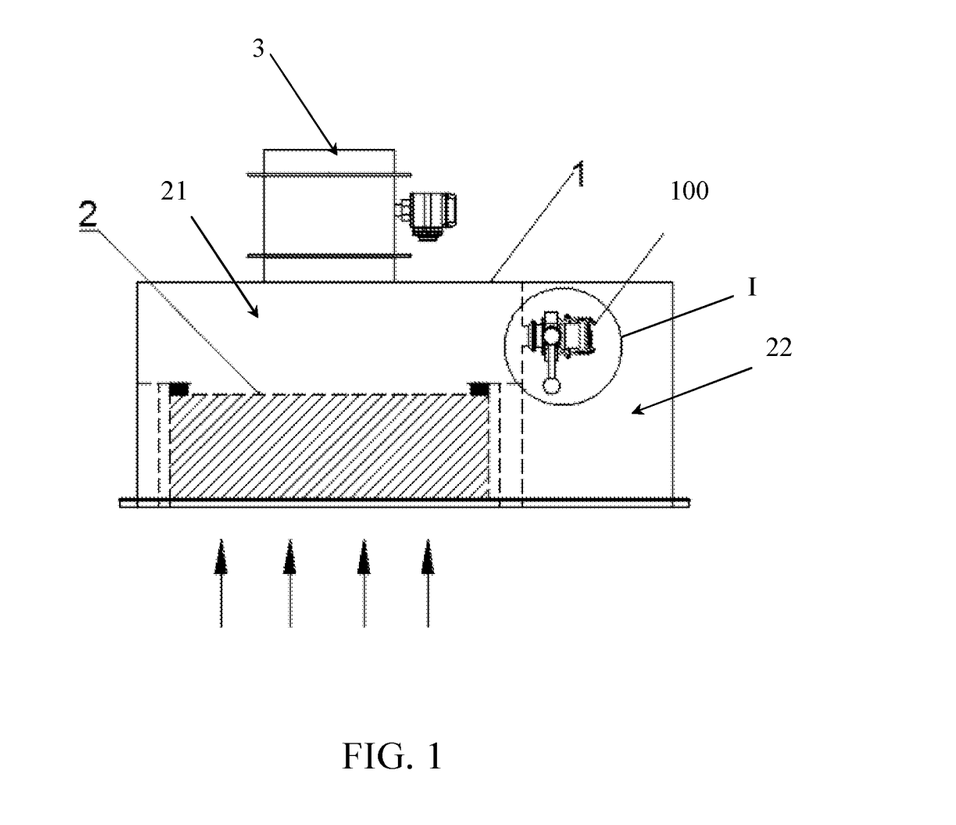
FIG. 1 is a schematic structural view of Embodiment 1 of a device for filtering biologically contaminated air provided in the present invention, where a tuyere box is used.

The first chamber 21 is a hollow and sealed box. A HEPA filter 2 is disposed on an inner side at the bottom of the first chamber 21. The HEPA filter 2 is a device that is configured to capture particles in air and has filtration efficiency greater than 99.95%, and mainly includes a filter element and a housing. An air inlet is provided at the bottom of the HEPA filter 2, an air outlet is provided at the top of the HEPA filter 2, and high-efficiency filter media are spaced apart between the air inlet and the air outlet.

A vent hole is opened at a position corresponding to the air inlet on a bottom surface of the first chamber 21. The vent hole and the air inlet are in communication with an external space that needs air filtering (for example, a laboratory). The arrow direction below the first chamber 21 is the direction in which an airflow enters a laboratory in FIG. 1.

The second chamber 22 is a hollow and sealed box. A unit 100 for validating an in situ decontamination effect is installed on a left sidewall of the second chamber 22. The unit 100 for validating an in situ decontamination effect is in communication with the first chamber 21. The unit 100 for validating an in situ decontamination effect is configured to validate an actual decontamination effect of the HEPA filter that needs to perform gas decontamination 2. That is, the object to be validated is the HEPA filter 2 that has previously performed gas decontamination (a gas disinfectant is used to perform decontamination), so as to validate an actual decontamination effect of the HEPA filter 2. In the present invention, in a specific implementation, an air outlet is provided at the top of the first chamber 21. The air outlet is in communication with an isolation damper 3. The isolation damper 3 is mainly configured to turn off the device for filtering biologically contaminated air and close a ventilation pipe, so as to isolate a laboratory in which the device for filtering biologically contaminated air is located from the external environment.

In the present invention, it should be noted that, the HEPA filter is any air filter whose filtration efficiency for particles with most penetrating particle sizes (a specific range of the particle sizes may be 0.1 μm to 0.2 μm) is not less than 99.95%.

In the present invention, it should be noted that, the HEPA filter 2 is mainly configured to filter and intercept biological aerosols in air. The isolation damper 3 is mainly configured to turn off a pipe passage, to enable a box installed with the HEPA filter to form a sealed box, so as to facilitate decontamination.

In the present invention, in a specific implementation, the unit 100 for validating an in situ decontamination effect is in communication with a right-side inner wall of the first chamber 21.

Figure 2:
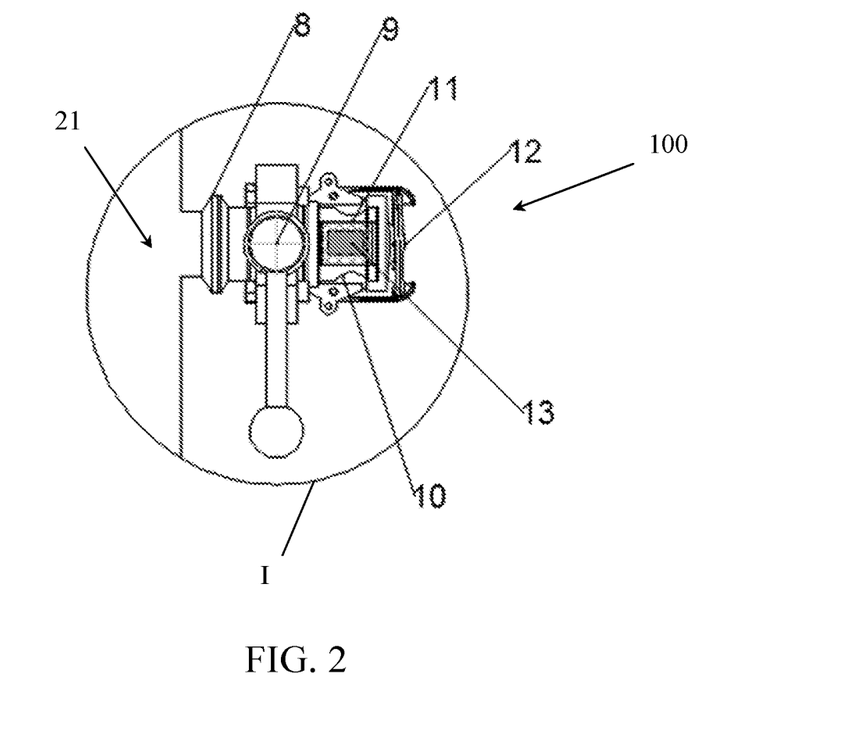
FIG. 2 is a schematic enlarged view of a decontamination validation unit of the part I in FIG. 1.
Figure 3:
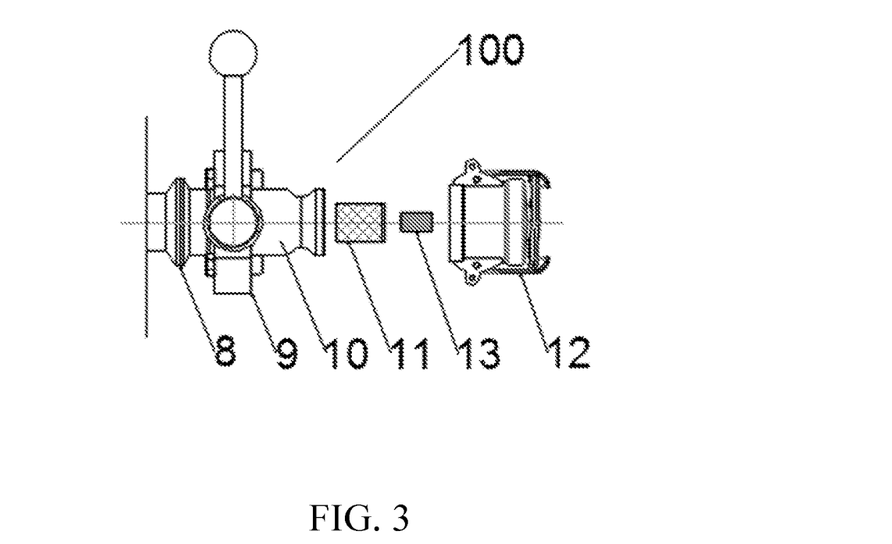
FIG. 3 is a three-dimensional schematic exploded view of a unit for validating an in situ decontamination effect provided in the present invention, and is also a three-dimensional schematic exploded view of a unit for validating an in situ decontamination effect in the device for filtering biologically contaminated air provided in the present invention shown in FIG. 1.

Referring to both FIG. 2 and FIG. 3, for the present invention, the unit 100 for validating an in situ decontamination effect includes a connecting end 8. A left end of the connecting end 8 is in communication with the right-side inner wall of the first chamber 21. A right end of the connecting end 8 is connected to a closed isolation damper 9. A right end of the closed isolation damper 9 is connected to a hollow decontamination validation chamber 10. A sealing cover 12 is sleeved over an outer wall of the decontamination validation chamber 10. Therefore, the sealing cover 12 may be used to seal the decontamination validation chamber 10 for isolation from the external environment.

It should be noted that, in the present invention, referring to FIG. 3, the unit 100 for validating an in situ decontamination effect provided in the present invention is not limited to being in communication with the first chamber 21, or may further be in communication with any space that needs gas decontamination, to validate actual decontamination effects of these spaces. In a specific implementation, the left end of the connecting end 8 is in communication with any space (for example, the first chamber and another chamber that has undergone gas decontamination) that needs gas decontamination.

In the present invention, a mesh cup 11 is placed inside the decontamination validation chamber 10. The mesh cup 11 is used for placing a bioindicator 13 that can validate a decontamination effect. In a specific implementation, the bioindicator 13 may be, for example, a *Bacillus subtilis* tablet.

It should be noted that, the mesh cup may alternatively be replaced with another device that can fix the bioindicator.

It should be noted that, in a normal operation state of the present invention, the closed isolation damper 9 is in a turned-off state, the mesh cup 11 is placed inside the decontamination validation chamber 10, and the sealing cover 12 is installed on the decontamination validation chamber 10 and is in a sealed state.

Figure 4:
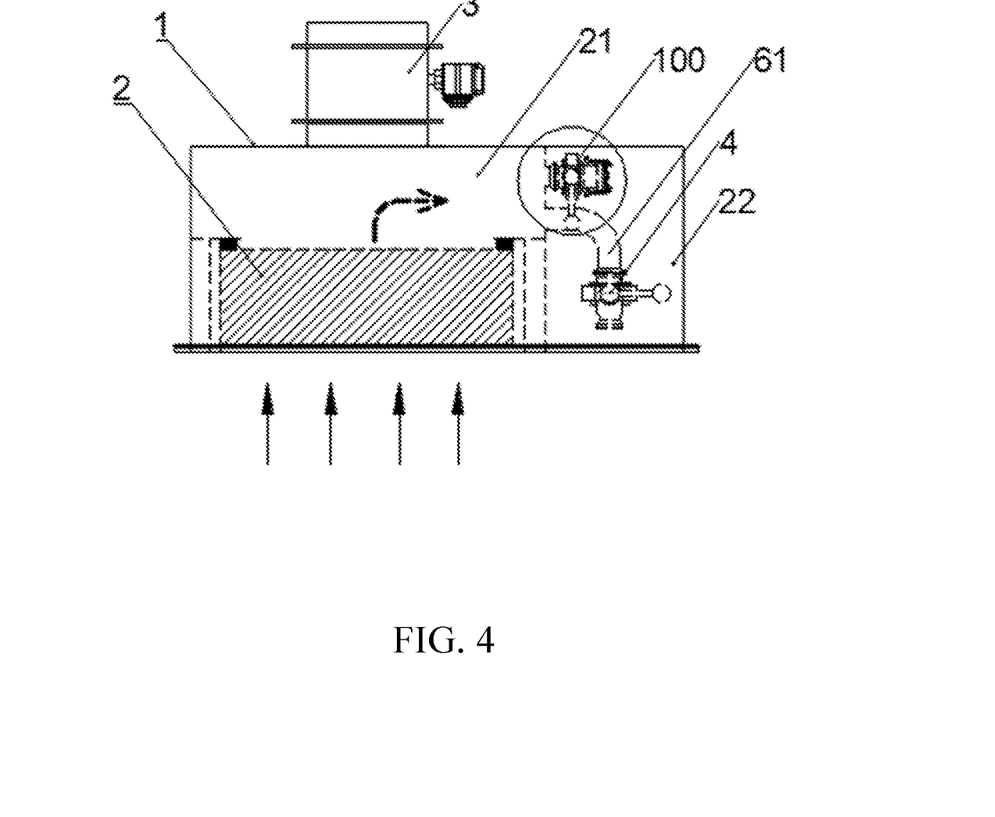
FIG. 4 is a schematic structural view of Embodiment 2 of a device for filtering biologically contaminated air provided in the present invention, where a tuyere box is used.
Figure 5:
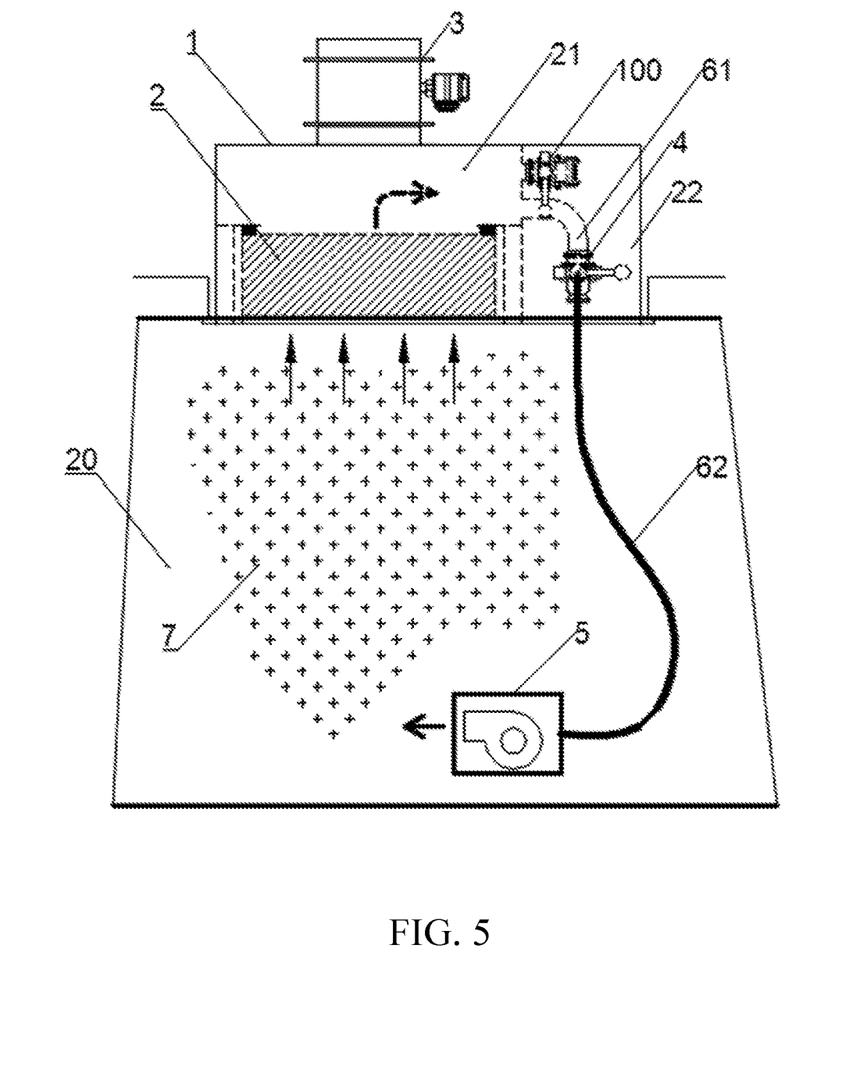
FIG. 5 is a schematic structural view of Embodiment 3 of a device for filtering biologically contaminated air provided in the present invention, where a tuyere box is used.

Referring to both FIG. 4 and FIG. 5, in a specific implementation, the present invention is not limited to the validation of the decontamination effect of the HEPA filter after gas decontamination, and may further have a function of performing in situ gas decontamination on the HEPA filter 2. Referring to FIG. 4 and FIG. 5, the left sidewall of the second chamber 22 is further in communication with a first gas decontamination tube 61. A left end of the first gas decontamination tube 61 is in communication with the first chamber 21. A right end of the first gas decontamination tube 61 is in communication with an upper end of a second gas decontamination tube 62 through a first gas decontamination interface 4. A lower end of the second gas decontamination tube 62 is in communication with an air circulation drive device 5 (which may be specifically, for example, a fan or an air pump). The air circulation drive device 5 is located in the external space that needs air filtering (a laboratory 20 shown in FIG. 5). During decontamination, the air circulation drive device 5 may pump air inside the first chamber 21 into the laboratory. At the same time, a decontamination gas inside the laboratory may penetrate the HEPA filter 2 again to enter the first chamber 21, to enable the decontamination gas to continuously penetrate the HEPA filter 2, so as to eventually achieve the objective of decontamination and sterilization.

For the present invention, referring to FIG. 4 and FIG. 5, to perform in situ gas decontamination on the HEPA filter 2 located in the tuyere box, a specific operation method is as follows:

Step 1: Turn off the isolation damper 3 connected to the air outlet located at the top of the first chamber 21, connect the air circulation drive device 5 to the first gas decontamination interface 4, and connect the HEPA filter 2 to the external space that needs air filtering (the laboratory 20 shown in FIG. 4).

Step 2: Turn on the air circulation drive device 5, and turn off all passages of the laboratory 20, so that the air inside the laboratory 20 sequentially passes through the vent hole on the bottom surface of the first chamber 21 and the filter media of the high efficiency filter, then passes through the first gas decontamination tube 61, the first gas decontamination interface 4, the second gas decontamination tube 62, and the air circulation drive device 5, and is eventually discharged into the laboratory 20.

Step 3: A user releases a gas disinfectant 7 (the gas disinfectant may be specifically gaseous chlorine dioxide, gaseous hydrogen peroxide or the like) in the laboratory 20, so that the laboratory 20 is filled with the gas disinfectant 7, and under the effect of the air circulation drive device 5, the gas disinfectant 7 may continuously penetrate the HEPA filter 2 in the device for filtering biologically contaminated air. Therefore, by means of the present invention, not only in situ gas decontamination of the HEPA filter 2 can be performed, but also gas decontamination of the laboratory 20 is performed, that is, the HEPA filter 2 and the laboratory 20 are synchronously decontaminated.

For the present invention, referring to FIG. 1 to FIG. 3, to reliably validate the decontamination effect of the HEPA filter 2 at the same time when in situ gas decontamination of the HEPA filter 2 is performed, a specific operation procedure of validating the decontamination effect is as follows:

First, before decontamination begins, remove the sealing cover 12 in the unit 100 for validating an in situ decontamination effect (in this case, the closed isolation damper 9 is in a turned-off state), take out the mesh cup 11 from the decontamination validation chamber 10 of the unit 100 for validating an in situ decontamination effect, and place the bioindicator 13 (for example, a *Bacillus subtilis* tablet) in the mesh cup 11.

Then, place the mesh cup 11 in the decontamination validation chamber 10, and install the sealing cover 12 on the decontamination validation chamber 10.

Subsequently, open the closed isolation damper 9 of the unit 100 for validating an in situ decontamination effect, to connect the decontamination validation chamber 10 to the first chamber 21 in the device for filtering biologically contaminated air, and turn on the air circulation drive device 5 to perform decontamination, so that during decontamination, the unit 100 for validating an in situ decontamination effect validates a decontamination effect at the same time.

After a decontamination procedure ends, discharge the residual gas disinfectant 7 in the laboratory 20, turn off the closed isolation damper 9 of the unit 100 for validating an in situ decontamination effect, open the sealing cover 12, take out the bioindicator 13, perform subsequent culturing, and determine an decontamination and sterilization effect. By using positive control, when the culturing has a negative result, decontamination succeeds.

It should be noted that, according to the regulation in the Technical Specifications for Decontamination (Version 2002) published by the Ministry of Health, common indicator bacteria in air decontamination includes *Staphylococcus albus*, black variant spores of *Bacillus subtilis*, and the like. In actual evaluation of decontamination, a filter paper sheet or a stainless steel sheet is used as a carrier for bacteria or endospores, and a suspension of the bacteria is dropped on the carrier to manufacture the bioindicator 13 (that is, a tablet). The tablet may be self-made or purchased. Domestic and foreign tablets, for example, tablets produced by Sihuan Bioengineering Co., Ltd, are commercially available.

After tablets are prepared, and before decontamination, experimental groups need to be provided as follows: a decontamination group, a positive control group, and a negative control group. The decontamination group needs to be placed in the device in this patent for decontamination and evaluation. For the decontamination group, the bioindicator 13 (that is, the tablet) is decontaminated. For the positive control group, the tablet is not decontaminated.

After decontamination ends, subsequent treatment needs to be performed on the tablets of the decontamination group and the positive control group according to the regulation in the existing Technical Specifications for the Decontamination in Medical Institutions (Version 2002). The subsequent treatment generally includes the following steps:

Step 1: Place the decontaminated tablet or the tablet in a blank group separately in a sterile eluent for elution.

Step 2: Take 1 mL of the eluent and place the 1 mL of the eluent in a sterile flat dish, add a culture medium that is cooled to 55 degrees, and wait for solidification.

Step 3: Place the flat dish in the second step into a culture box with a constant temperature of 37 degrees to perform culturing for 24 h to 48 h, and then take out the flat dish and count the bacteria.

Step 4: For the negative control group, add a blank eluent to a flat dish, then add a culture medium, and perform operations and culturing according to the same steps. The step is to prove that the used reagents are sterile and the related operations are sterile operations. No bacteria grows in the flat dish of the negative control group, and it is proven that the experiment is valid.

Step 5: Result calculation. The result obtained in the positive control group is a blank-group bacterial colony count, and the result obtained in the decontamination group is a decontamination-group bacterial colony count.

The formula for calculating the decontamination efficiency is as follows:

sterilization logarithmic value=lg(blank-group bacterial colony count)−lg(decontamination-group bacterial colony count)

According to the regulation in the Technical Specifications for the Decontamination in Medical Institutions (Version 2002), when the sterilization logarithmic value is greater than 4, the decontamination is efficient and succeeds. When the sterilization logarithmic value is greater than 6, a sterilization level is reached. If the sterilization logarithmic value is less than or equal to 6, it indicates that sterilization does not succeed.

It should be noted that the device for filtering biologically contaminated air provided in the present invention has high performance of biosafety protection. An airtight design is used for the structure and accessory equipment of the device for filtering biologically contaminated air, and the entire device has desirable performance of mechanical isolation.

Figure 6:
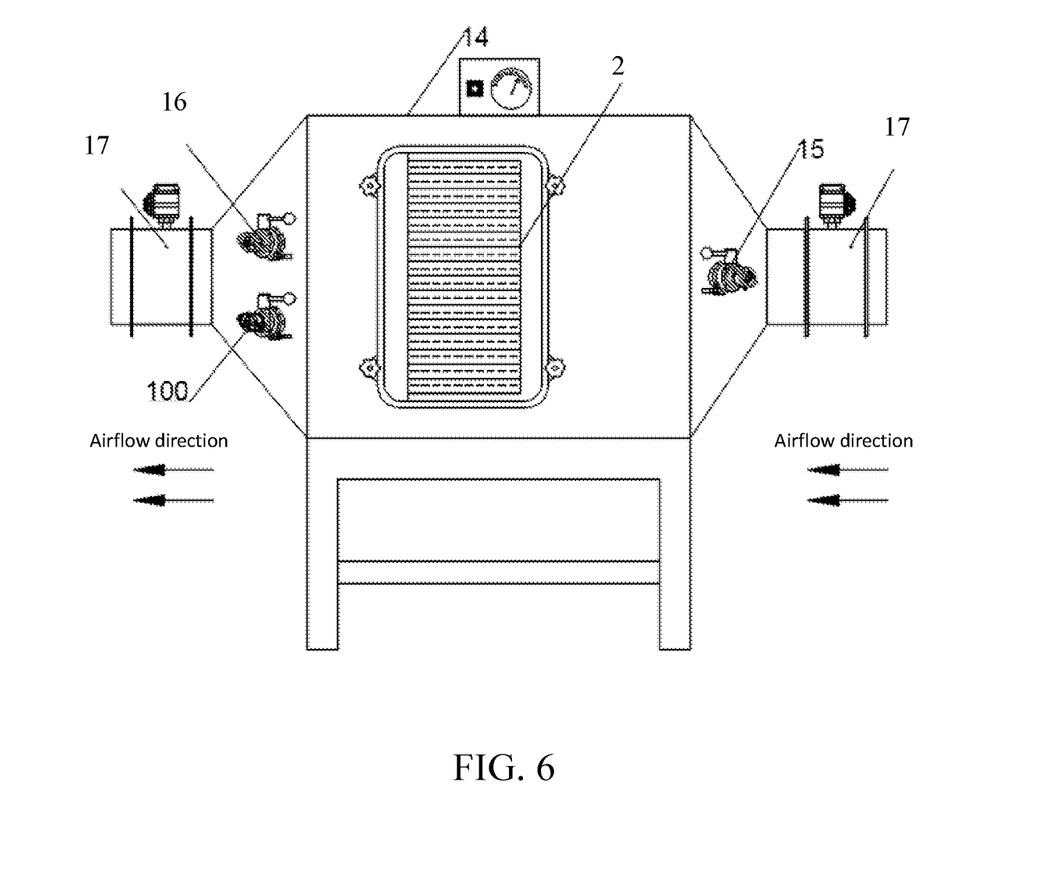
FIG. 6 is a schematic structural view of Embodiment 4 of a device for filtering biologically contaminated air provided in the present invention, where a box body is used.

Referring to FIG. 6, the unit for validating an in situ decontamination effect provided in the present invention is not limited to being applied to the device for filtering biologically contaminated air having the HEPA filter installed in the tuyere box shown in FIG. 1, and may further be applied to the device for filtering biologically contaminated air having a HEPA filter installed in a box body. As shown in FIG. 6, the device for filtering biologically contaminated air includes a hollow and sealed box body 14. A left end and a right end of the box body 14 are respectively in communication with an airtight isolation damper 17. The airtight isolation damper 17 is configured to isolate the internal space of the box body 14 from the external environment.

One HEPA filter 2 is disposed on a front surface in the middle of the box body 14. The HEPA filter 2 is a device that is configured to capture particles in air and has filtration efficiency greater than 99.95%, and mainly includes a filter element and a housing.

A second gas decontamination joint outlet 16 and a second gas decontamination joint inlet 15 are further respectively disposed at positions on a left side and a right side of the HEPA filter 2 of the front surface of the box body 14. One unit 100 for validating an in situ decontamination effect is further disposed at a position below the second gas decontamination joint inlet 15 on the front surface of the box body 14. The unit 100 for validating an in situ decontamination effect is connected to the box body 14.

Referring to FIG. 3, for the device for filtering biologically contaminated air having the HEPA filter installed in the box body, the structure of the unit 100 for validating an in situ decontamination effect is similarly shown in FIG. 3. Refer to the foregoing description for details, which are no longer described herein.

Similarly, it should be noted that, based on the foregoing working principle of performing in situ gas decontamination on the HEPA filter 2 installed in the tuyere box and the operation principle of validating the decontamination effect of the in situ gas decontamination, in situ gas decontamination of the HEPA filter 2 installed in the box body may be similarly performed, and after the in situ gas decontamination is performed, the decontamination effect of the HEPA filter 2 is reliably validated.

In conclusion, compared with the prior art, by means of the unit for validating an in situ decontamination effect and the device for filtering biologically contaminated air to which the unit is applied provided in the present invention, an actual decontamination effect of a HEPA filter after gas decontamination can be validated reliably in time, thereby effectively preventing pathogenic microorganisms that exist on the surface of the HEPA filter from spreading outside a biosafety facility such as a laboratory, avoiding polluting the external environment of the biosafety facility such as a laboratory, ensuring personal safety, and eliminating the possibility of a major public health event, which is greatly significant in production practice.

In addition, by means of the unit for validating an in situ decontamination effect and the device for filtering biologically contaminated air to which the unit is applied provided in the present invention, a decontamination effect of a HEPA filter after gas decontamination can be validated reliably in time, and at the same time the function of performing in situ gas decontamination on the HEPA filter is further provided, so as to effectively perform gas decontamination on the HEPA filter and synchronously implement the decontamination of a biosafety facility such as a laboratory connected to the HEPA filter.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A unit for validating an in situ decontamination effect, comprising a connecting end (8), wherein a left end of the connecting end (8) is in communication with any space that needs gas decontamination;
    a right end of the connecting end (8) is connected to a closed isolation damper (9), a right end of the closed isolation damper (9) is connected to a hollow decontamination validation chamber (10), and a sealing cover (12) is sleeved over an outer wall of the decontamination validation chamber (10); and
    the decontamination validation chamber (10) is used for placing a bioindicator (13).

2. The device for filtering biologically contaminated air according to claim 1, wherein a mesh cup (11) is placed inside the decontamination validation chamber (10), and the mesh cup (11) is used for placing the bioindicator (13).

3. A device for filtering biologically contaminated air, comprising a unit (100) for validating an in situ decontamination effect and a hollow box installed with a high efficiency particulate air (HEPA) filter (2), wherein
    the unit (100) for validating an in situ decontamination effect is in communication with the hollow box;
    the unit for validating an in situ decontamination effect, comprising a connecting end (8), wherein a left end of the connecting end (8) is in communication with any space that needs gas decontamination;
    a right end of the connecting end (8) is connected to a closed isolation damper (9), a right end of the closed isolation damper (9) is connected to a hollow decontamination validation chamber (10), and a sealing cover (12) is sleeved over an outer wall of the decontamination validation chamber (10); and
    the decontamination validation chamber (10) is used for placing a bioindicator (13).

4. The device for filtering biologically contaminated air according to claim 3, wherein the hollow box is a tuyere box (1), and the tuyere box (1) comprises a first chamber (21) and a second chamber (22) that are transversely distributed;
    the HEPA filter (2) is disposed on an inner side at the bottom of the first chamber (21), and the HEPA filter (2) is in communication with an external space that needs air filtering; and
    the unit (100) for validating an in situ decontamination effect is installed on a left sidewall of the second chamber (22), the unit (100) for validating an in situ decontamination effect is in communication with the first chamber (21), and the unit (100) for validating an in situ decontamination effect is configured to validate a decontamination effect of the HEPA filter that needs to perform gas decontamination (2).

5. The device for filtering biologically contaminated air according to claim 4, wherein an air inlet is provided at the bottom of the HEPA filter (2), an air outlet is provided at the top of the HEPA filter (2), and high-efficiency filter media are spaced apart between the air inlet and the air outlet; and a vent hole is opened at a position corresponding to the air inlet on a bottom surface of the first chamber (21), and the vent hole and the air inlet are in communication with the external space that needs air filtering.

6. The device for filtering biologically contaminated air according claim 5, wherein the unit (100) for validating an in situ decontamination effect comprises a connecting end (8), a left end of the connecting end (8) is in communication with the right-side inner wall of the first chamber (21), a right end of the connecting end (8) is connected to a closed isolation damper (9), a right end of the closed isolation damper (9) is connected to a hollow decontamination validation chamber (10), and a sealing cover (12) is sleeved over an outer wall of the decontamination validation chamber (10); and
    a mesh cup (11) is placed inside the decontamination validation chamber (10), and the mesh cup (11) is used for placing a bioindicator (13).

7. The device for filtering biologically contaminated air according to claim 6, wherein the left sidewall of the second chamber (22) is further in communication with a first gas decontamination tube (61), a left end of the first gas decontamination tube (61) is in communication with the first chamber (21), a right end of the first gas decontamination tube (61) is in communication with an upper end of a second gas decontamination tube (62) through a first gas decontamination interface (4), a lower end of the second gas decontamination tube (62) is in communication with an air circulation drive device (5), and the air circulation drive device (5) is located in the external space that needs air filtering; and
    the air circulation drive device (5) is a fan or an air pump.

8. The device for filtering biologically contaminated air according to claim 4, wherein an air outlet is provided at the top of the first chamber (21), and the air outlet is in communication with an isolation damper (3).

9. The device for filtering biologically contaminated air according to claim 8, wherein the unit (100) for validating an in situ decontamination effect comprises a connecting end (8), a left end of the connecting end (8) is in communication with the right-side inner wall of the first chamber (21), a right end of the connecting end (8) is connected to a closed isolation damper (9), a right end of the closed isolation damper (9) is connected to a hollow decontamination validation chamber (10), and a sealing cover (12) is sleeved over an outer wall of the decontamination validation chamber (10); and a mesh cup (11) is placed inside the decontamination validation chamber (10), and the mesh cup (11) is used for placing a bioindicator (13).

10. The device for filtering biologically contaminated air according to claim 9, wherein the left sidewall of the second chamber (22) is further in communication with a first gas decontamination tube (61), a left end of the first gas decontamination tube (61) is in communication with the first chamber (21), a right end of the first gas decontamination tube (61) is in communication with an upper end of a second gas decontamination tube (62) through a first gas decontamination interface (4), a lower end of the second gas decontamination tube (62) is in communication with an air circulation drive device (5), and the air circulation drive device (5) is located in the external space that needs air filtering; and the air circulation drive device (5) is a fan or an air pump.

11. The device for filtering biologically contaminated air according to claim 4, wherein the unit (100) for validating an in situ decontamination effect is in communication with a right-side inner wall of the first chamber (21).

12. The device for filtering biologically contaminated air according to claim 11, wherein the unit (100) for validating an in situ decontamination effect comprises a connecting end (8), a left end of the connecting end (8) is in communication with the right-side inner wall of the first chamber (21), a right end of the connecting end (8) is connected to a closed isolation damper (9), a right end of the closed isolation damper (9) is connected to a hollow decontamination validation chamber (10), and a sealing cover (12) is sleeved over an outer wall of the decontamination validation chamber (10); and a mesh cup (11) is placed inside the decontamination validation chamber (10), and the mesh cup (11) is used for placing a bioindicator (13).

13. The device for filtering biologically contaminated air according to claim 12, wherein the left sidewall of the second chamber (22) is further in communication with a first gas decontamination tube (61), a left end of the first gas decontamination tube (61) is in communication with the first chamber (21), a right end of the first gas decontamination tube (61) is in communication with an upper end of a second gas decontamination tube (62) through a first gas decontamination interface (4), a lower end of the second gas decontamination tube (62) is in communication with an air circulation drive device (5), and the air circulation drive device (5) is located in the external space that needs air filtering; and the air circulation drive device (5) is a fan or an air pump.

14. The device for filtering biologically contaminated air according to claim 4, wherein the unit (100) for validating an in situ decontamination effect comprises a connecting end (8), a left end of the connecting end (8) is in communication with the right-side inner wall of the first chamber (21), a right end of the connecting end (8) is connected to a closed isolation damper (9), a right end of the closed isolation damper (9) is connected to a hollow decontamination validation chamber (10), and a sealing cover (12) is sleeved over an outer wall of the decontamination validation chamber (10); and a mesh cup (11) is placed inside the decontamination validation chamber (10), and the mesh cup (11) is used for placing a bioindicator (13).

15. The device for filtering biologically contaminated air according to claim 14, wherein the left sidewall of the second chamber (22) is further in communication with a first gas decontamination tube (61), a left end of the first gas decontamination tube (61) is in communication with the first chamber (21), a right end of the first gas decontamination tube (61) is in communication with an upper end of a second gas decontamination tube (62) through a first gas decontamination interface (4), a lower end of the second gas decontamination tube (62) is in communication with an air circulation drive device (5), and the air circulation drive device (5) is located in the external space that needs air filtering; and the air circulation drive device (5) is a fan or an air pump.

16. The device for filtering biologically contaminated air according to claim 3, wherein the unit (100) for validating an in situ decontamination effect comprises a connecting end (8), a left end of the connecting end (8) is in communication with the right-side inner wall of the first chamber (21), a right end of the connecting end (8) is connected to a closed isolation damper (9), a right end of the closed isolation damper (9) is connected to a hollow decontamination validation chamber (10), and a sealing cover (12) is sleeved over an outer wall of the decontamination validation chamber (10); and a mesh cup (11) is placed inside the decontamination validation chamber (10), and the mesh cup (11) is used for placing a bioindicator (13).

17. The device for filtering biologically contaminated air according to claim 16, wherein the left sidewall of the second chamber (22) is further in communication with a first gas decontamination tube (61), a left end of the first gas decontamination tube (61) is in communication with the first chamber (21), a right end of the first gas decontamination tube (61) is in communication with an upper end of a second gas decontamination tube (62) through a first gas decontamination interface (4), a lower end of the second gas decontamination tube (62) is in communication with an air circulation drive device (5), and the air circulation drive device (5) is located in the external space that needs air filtering; and the air circulation drive device (5) is a fan or an air pump.

18. The device for filtering biologically contaminated air according to claim 3, wherein the hollow box is a box body (14), and a left end and a right end of the box body (14) are respectively in communication with an airtight isolation damper (17);

the HEPA filter (2) is disposed on a front surface in the middle of the box body (14); and a second gas decontamination joint outlet (16) and a second gas decontamination joint inlet (15) are further respectively disposed at positions on a left side and a right side of the HEPA filter (2) of the front surface of the box body (14), and one unit (100) for validating an in situ decontamination effect is further disposed at a position below the second gas decontamination joint inlet (15) on the front surface of the box body (14).

* * * * *